(12) United States Patent
Pitts

(10) Patent No.: US 7,798,663 B1
(45) Date of Patent: Sep. 21, 2010

(54) DOMESTIC DEVICE

(76) Inventor: David M. Pitts, 1417 SW. 33rd St., Oklahoma City, OK (US) 73119

( * ) Notice: Subject to any disclaimer, the term of this patent is extended or adjusted under 35 U.S.C. 154(b) by 372 days.

(21) Appl. No.: 12/041,225

(22) Filed: Mar. 3, 2008

(51) Int. Cl.
B03C 3/41 (2006.01)
(52) U.S. Cl. .......................................... 362/96; 362/410
(58) Field of Classification Search ................... 362/96, 362/410, 810
See application file for complete search history.

(56) References Cited

U.S. PATENT DOCUMENTS

| 1,357,824 | A | 11/1920 | Rhodes |
| 3,711,698 | A | 1/1973 | Hess |
| 3,959,642 | A | 5/1976 | Turro |
| 5,392,379 | A | 2/1995 | Fussell |
| D504,842 | S | 5/2005 | Umeda et al. |
| 2004/0136888 | A1 | 7/2004 | Shimizu et al. |

Primary Examiner—Jason Moon Han
Assistant Examiner—Sean P Gramling
(74) Attorney, Agent, or Firm—Crossley Patent Law; Mark A. Crossley

(57) ABSTRACT

A domestic device that serves as both a night-light and an incense burner. The device has a base with a shelf circumferentially surrounding the base. The shelf includes both a number of incense stick holders and a number of incense cone supports. A light is located within the base, with the light being powered by standard household current and controlled by an on/off switch attached to the base. A conically-shaped cover is placed over the base, with the cover having a series of vent holes to allow dispersion of both light and heat from the electric light and emitted scent from any incense located on the base.

10 Claims, 5 Drawing Sheets

US 7,798,663 B1

DOMESTIC DEVICE

BACKGROUND OF THE INVENTION

The present invention concerns that of a new and improved domestic device that serves as both a night-light and an incense burner.

SUMMARY OF THE INVENTION

The present invention concerns that of a new and improved domestic device that serves as both a night-light and an incense burner. The device has a base with a shelf circumferentially surrounding the base. The shelf includes both a number of incense stick holders and a number of incense cone supports. A light is located within the base, with the light being powered by standard household current and controlled by an on/off switch attached to the base. A conically-shaped cover is placed over the base, with the cover having a series of vent holes to allow dispersion of both light and heat from the electric light and emitted scent from any incense located on the base.

There has thus been outlined, rather broadly, the more important features of a domestic device that the detailed description thereof that follows may be better understood and in order that the present contribution to the art may be better appreciated. There are, of course, additional features of the domestic device that will be described hereinafter and which will form the subject matter of the claims appended hereto.

In this respect, before explaining at least one embodiment of the domestic device in detail, it is to be understood that the domestic device is not limited in its application to the details of construction and to the arrangements of the components set forth in the following description or illustrated in the drawings. The domestic device is capable of other embodiments and being practiced and carried out in various ways. Also, it is to be understood that the phraseology and terminology employed herein are for the purpose of descriptions and should not be regarded as limiting.

As such, those skilled in the art will appreciate that the conception, upon which this disclosure is based, may readily be utilized as a basis for the designing of other structures, methods and systems for carrying out the several purposes of the present domestic device. It is important, therefore, that the claims be regarded as including such equivalent constructions insofar as they do not depart from the spirit and scope of the present invention.

It is therefore an object of the present invention to provide a domestic device which has all of the advantages of the prior art and none of the disadvantages.

It is another object of the present invention to provide a domestic device which may be easily and efficiently manufactured and marketed.

It is another object of the present invention to provide a domestic device which is of durable and reliable construction.

It is yet another object of the present invention to provide a domestic device which is economically affordable and available for relevant market segment of the purchasing public.

Other objects, features and advantages of the present invention will become more readily apparent from the following detailed description of the preferred embodiment when considered with the attached drawings and appended claims.

DESCRIPTION OF THE PREFERRED EMBODIMENT

Figure 1:
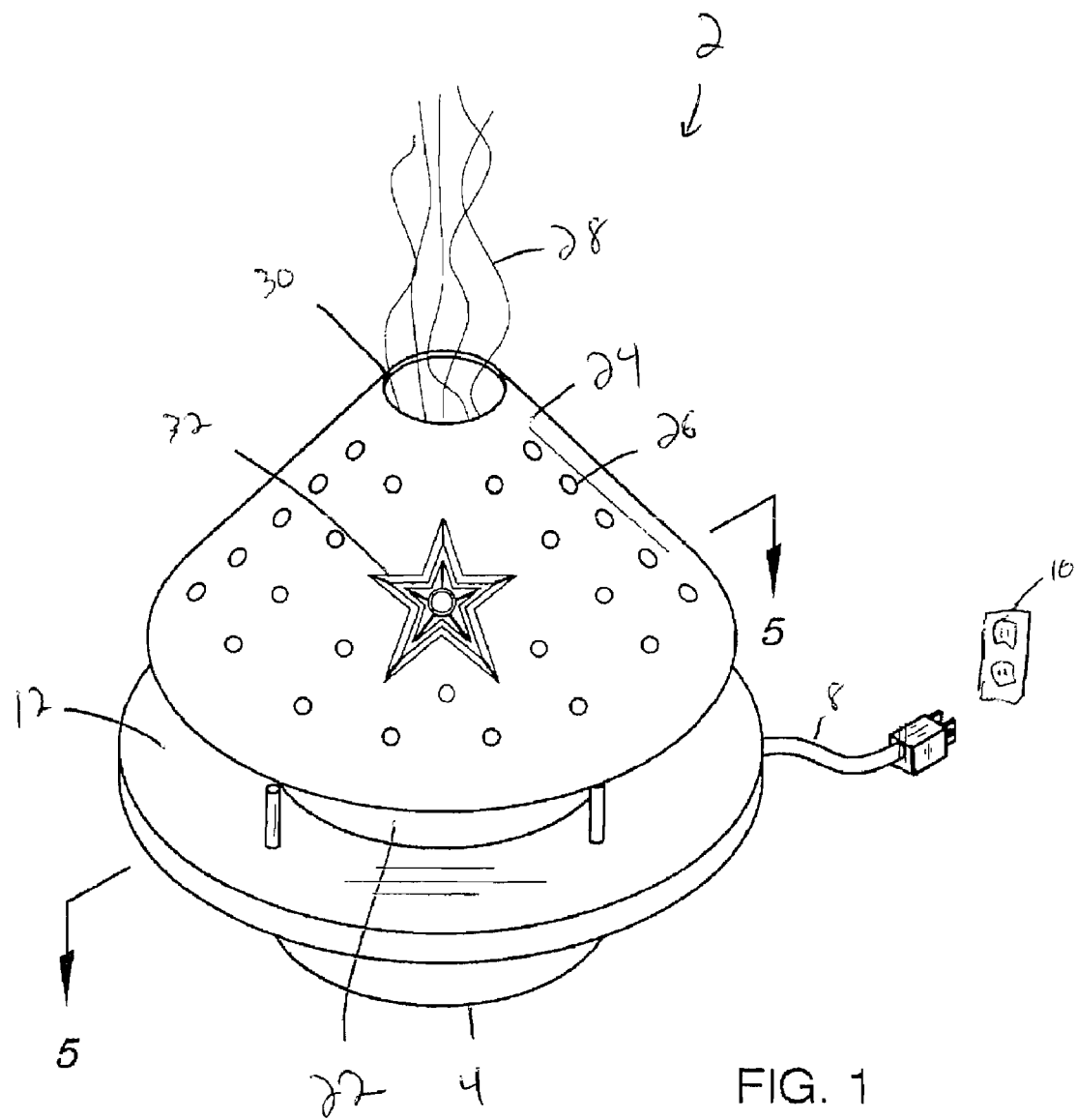
FIG. 1 shows a top perspective view of the domestic device.
Figure 2:
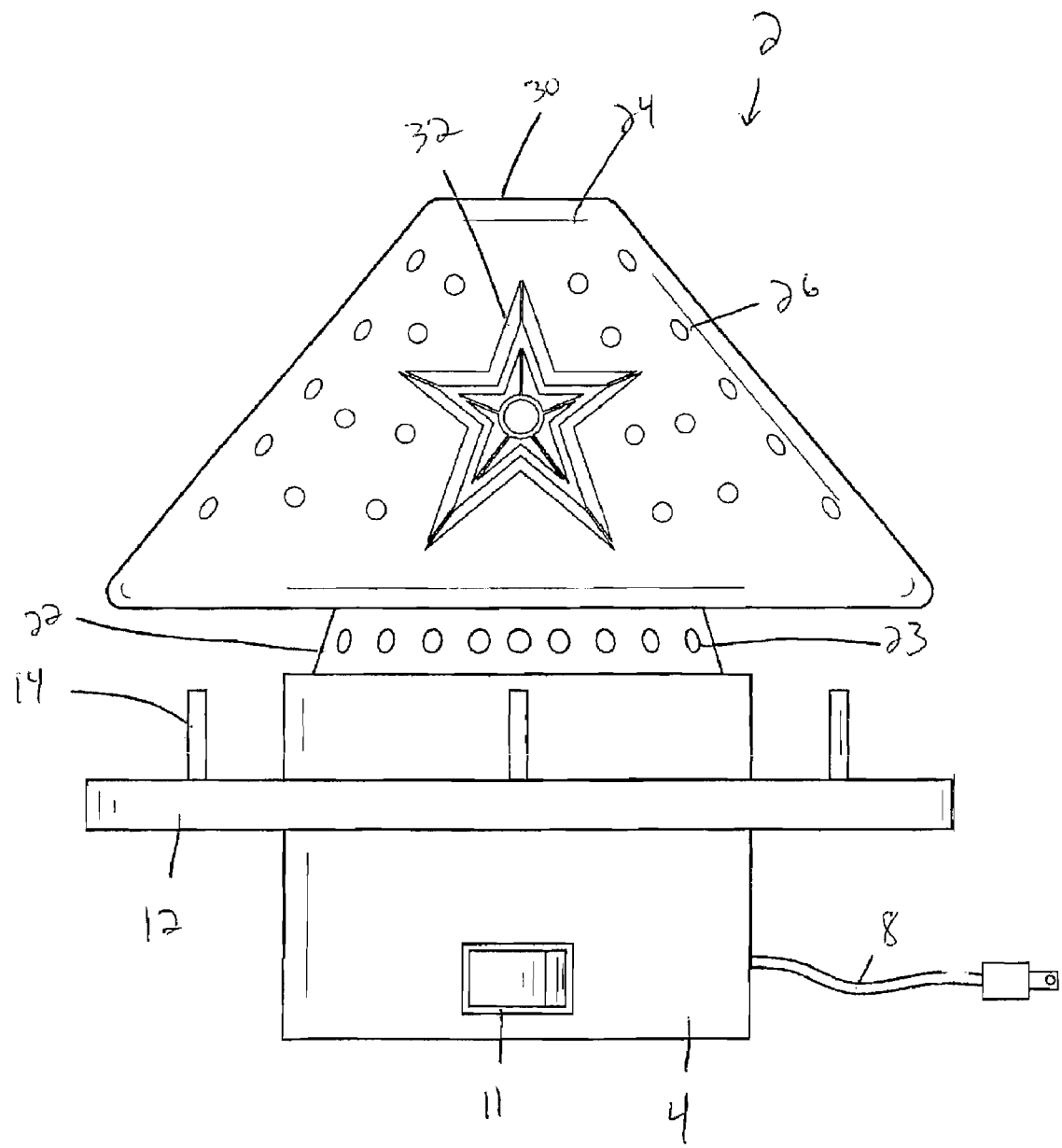
FIG. 2 shows a side view of the domestic device.
Figure 3:
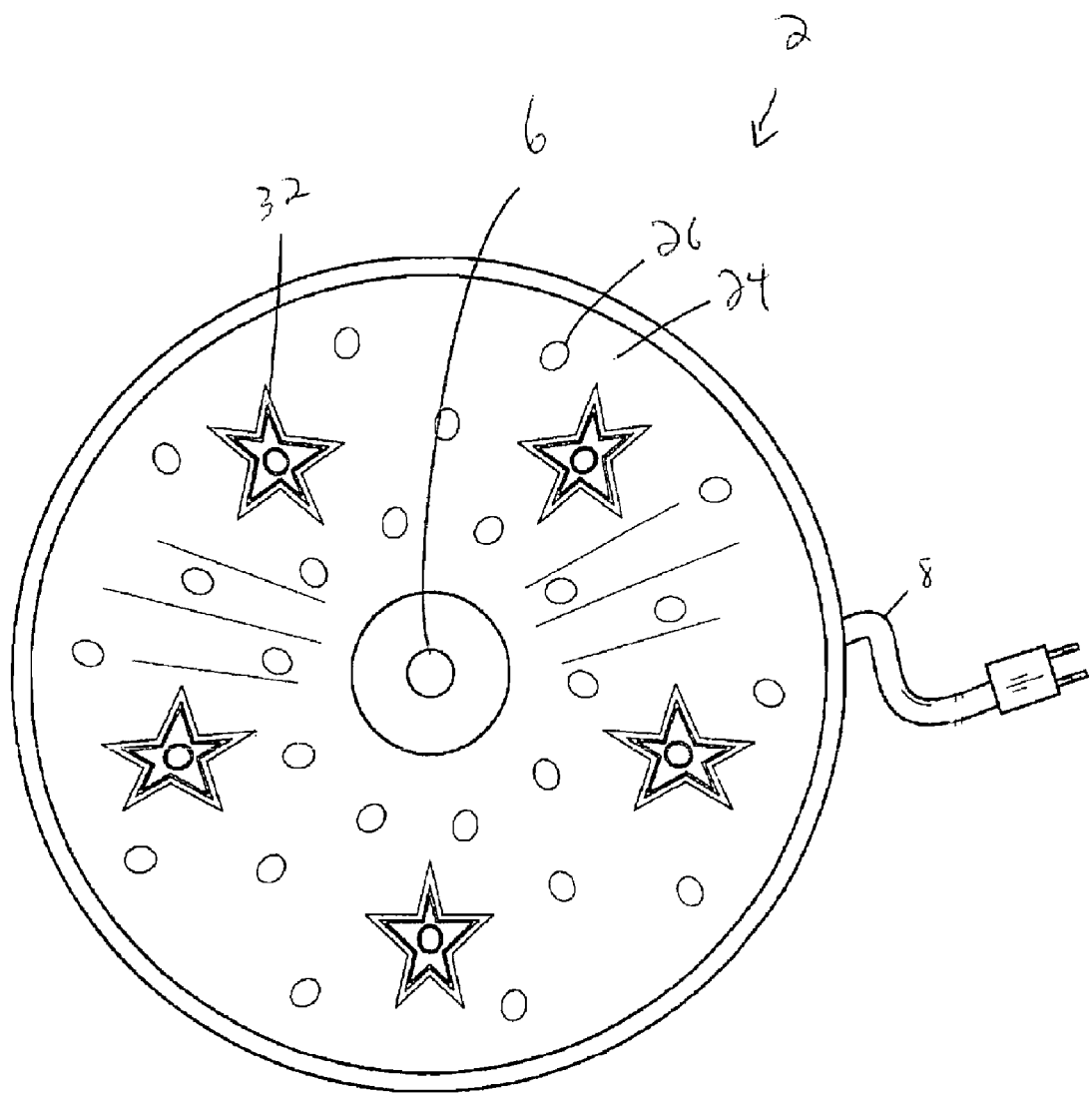
FIG. 3 shows a top view of the domestic device.
Figure 4:
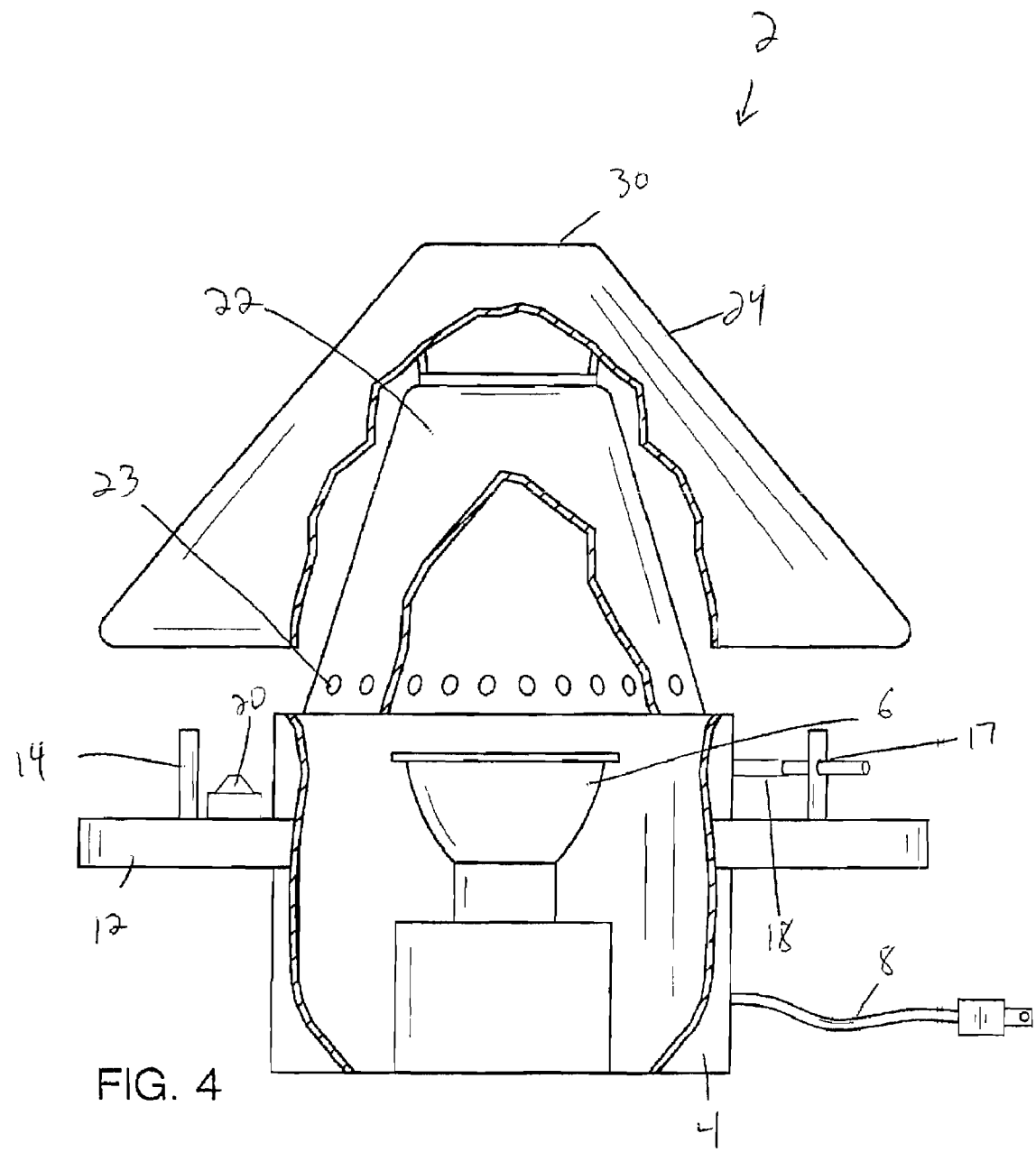
FIG. 4 shows a side cutaway view of the domestic device.
Figure 5:
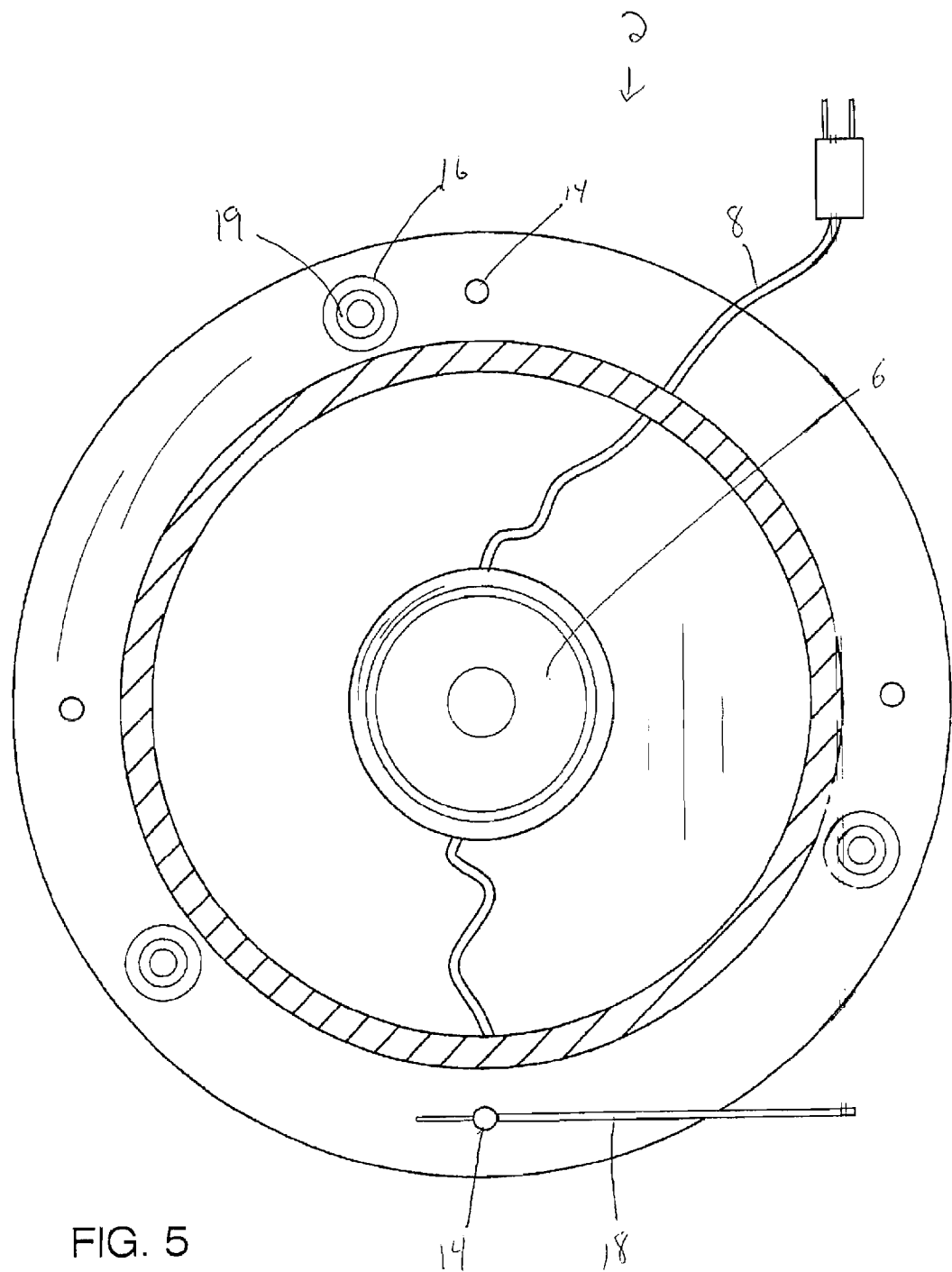
FIG. 5 shows a bottom view of the domestic device.

With reference now to the drawings, and in particular to FIGS. 1 through 5 thereof, a domestic device embodying the principles and concepts of the present invention and generally designated by the reference numeral 2 will be described.

As best illustrated in FIGS. 1 through 5, the domestic device 2 comprises a cylindrical base 4 that is hollow. The base 4 has an electrical light 6 located within it, with the light 6 being powered by an electrical cord 8 connected to standard household current 10. The light 6 is controlled by an on/off switch 11 that is attached to the base 4, with the on/off switch 11 serving as a circuit in between the standard household current 10 and the light 6. When the on/off switch 11 is in the "on" position, the circuit in between the light 6 and the standard household current 10 is closed, allowing the light 6 to receive power.

When the on/off switch is in the "off" position, however, the circuit in between the light 6 and the standard household current 10 is open, preventing the light 6 from receiving power.

A shelf 12 circumferentially surrounds the base 4 and includes a number of incense stick holders 14 and a number of incense cone supports 16. Each incense stick holder 14 has a hole 17 through which an incense stick 18 could be inserted. Furthermore, each incense cone support 16 is shaped in the manner of a slight cylindrical depression 19 to allow placement of an incense cone 20 for use.

A vertical support 22 is attached to the base 4, with the vertical support 22 being cylindrical in manner. The diameter of the vertical support 22 slowly decreases the further away from the base 4 that the vertical support 22 travels. The vertical support 22 includes a plurality of air holes 23 to allow for the dispersion of light and heat created from the light 6 located within the base 4.

A conically-shaped cover 24 is attached to the support 22, with the cover having a plurality of vent holes 26 evenly dispersed throughout it. The cover 24 essentially overlaps the entire surface area of the shelf 12, with the goal being to allow the scents 28 emitted from the incense sticks 14 and the incense cones 20 to be more evenly dispersed than if these scents were merely allowed to dispersed after being emitted from on top of the shelf 12.

Furthermore, the cover 24 has a centrally located hole 30 on it, with this hole 30 being located near the peak of the cover 24. The hole 30 allows an additional volume of scents 28 to be dispersed from the device 2 in a more even manner, and furthermore, helps to dispersed heat and light emitted from the electric light 6.

As an optional addendum, the cover 24 can have a number of designs 32 if desired.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

What I claim as my invention is:

1. A domestic device according to comprising
a base,
a light located within the base,
power means for providing power to the light,
control means for allowing power to be connected to the light located within the base, and
support means attached to the base to allow amounts of incense to be mounted,
dispersion means for dispersing the heat created by the light and scents created by incense that is connected to the base,
wherein the base has a cylindrical shape,
wherein the power means for providing power to the light further comprise
an amount of standard household current,
a cord connected to the standard household current, further wherein the cord is also connected to the light located within the base,
wherein the control means for allowing power to be connected to the light located within the base further comprises
a two-position switch attached to the base, said two-position switch having two positions comprising an "on" position and an "off" position,
wherein the two-position switch is connected to the cord and serves as a circuit in between the standard household current source and the light,
further wherein the switch serves as a closed circuit when the switch is in the "on" position, allowing power to travel from the standard household current source to the light,
further wherein the switch serves as an open circuit when the switch is in the "off" position, preventing power from traveling from the standard household current source to the light,
wherein the support means attached to the base to allow amounts of incense to be mounted further comprises
a shelf attached to the base, wherein the shelf circumferentially surrounds the base,
a plurality of incense stick holders attached to the shelf,
means for mounting an incense stick within the incense stick holder,
a plurality of incense cone supports attached to the shelf,
means for mounting an incense cone within each incense cone support.

2. A domestic device according to claim 1 wherein the means for mounting an incense stick within the incense stick holder further comprises
(a) a hole located within each incense stick holder,
(b) wherein a single incense stick can be inserted through the hole within each incense stick holder.

3. A domestic device according to claim 2 wherein the means for mounting an incense cone within each incense cone support further comprises
(a) a plurality of slight depressions located on the shelf,
(b) wherein an incense cone is placed on each slight depression located within the shelf.

4. A domestic device according to claim 3 wherein each slight depression located within the shelf is cylindrical.

5. A domestic device according to claim 4 wherein the dispersion means for dispersing the heat created by the light and scents created by incense that is connected to the base further comprises
(a) a vertical support attached to the base, the vertical support having a cylindrical shape,
(b) a first plurality of air holes located in the vertical support, wherein the first plurality of air holes are designed to allow for the dispersion of light and heat from the light located within the base,
(c) a cover attached to the vertical support,
(d) a second plurality of air holes located on the cover, and
(e) a central hole located on the cover.

6. A domestic device according to claim 5 wherein the cover attached to the vertical support is conically-shaped.

7. A domestic device according to claim 6 wherein the second plurality of air holes located on the cover are evenly dispersed on the cover.

8. A domestic device according to claim 7 wherein the cover overlaps the entire surface area of the shelf.

9. A domestic device according to claim 8 wherein the cover has a plurality of designs.

10. A domestic device comprising
(a) a base, the base having a cylindrical shape,
(b) a light located within the base,
(c) power means for providing power to the light, said power means further comprising (i) an amount of standard household current, and (ii) a cord connected to the standard household current, further wherein the cord is also connected to the light located within the base,
(d) control means for allowing power to be connected to the light located within the base, said control means further comprising (i) a two-position switch attached to the base, said two-position switch having two positions comprising an "on" position and an "off" position, (ii) wherein the two-position switch is connected to the cord and serves as a circuit in between the standard household current source and the light, (iii) further wherein the switch serves as a closed circuit when the switch is in the "on" position, allowing power to travel from the standard household current source to the light, (iv) further wherein the switch serves as an open circuit when the switch is in the "off" position, preventing power from traveling from the standard household current source to the light, and
(e) support means attached to the base to allow amounts of incense to be mounted, said support means further comprising (i) a shelf attached to the base, wherein the shelf circumferentially surrounds the base, (ii) a plurality of incense stick holders attached to the shelf, (iii) means for mounting an incense stick within the incense stick holder, said means further comprising (1) a hole located within each incense stick holder, (2) wherein a single incense stick can be inserted through the hole within each incense stick holder, (iv) a plurality of incense cone supports attached to the shelf, and (v) means for mounting an incense cone within each incense cone support, said means further comprising (1) a plurality of slight depressions located on the shelf, (2) wherein an incense cone is placed on each slight depression located within the shelf, each slight depression being cylindrical, and
(f) dispersion means for dispersing the heat created by the light and scents created by incense that is connected to the base, said dispersion means further comprising (i) a vertical support attached to the base, the vertical support having a cylindrical shape, (ii) a first plurality of air holes located in the vertical support, wherein the first plurality of air holes are designed to allow for the dispersion of light and heat from the light located within the base, (iii) a cover attached to the vertical support, the cover being conically-shaped, the cover overlapping the entire surface area of the shelf, (iv) a second plurality of air holes located on the cover, said second plurality of air holes being evenly dispersed on the cover, (v) a central hole located on the cover, and (vi) a plurality of designs attached to the cover.

* * * * *